United States Patent [19]

Schön et al.

[11] Patent Number: 5,226,465
[45] Date of Patent: Jul. 13, 1993

[54] MOUNTING DEVICE FOR MOTOR VEHICLE TIRES

[75] Inventors: Raimund Schön, Carpi; Tullio Gonzaga, Correggio, both of Italy

[73] Assignee: Stahlgruber Otto Gruber GmbH & Co., Fed. Rep. of Germany

[21] Appl. No.: 838,606

[22] Filed: Feb. 19, 1992

[30] Foreign Application Priority Data

Feb. 19, 1991 [DE] Fed. Rep. of Germany ............. 91019030[U]
Oct. 14, 1991 [DE] Fed. Rep. of Germany ... 9112783[U]

[51] Int. Cl.$^5$ .............................. B60C 25/07
[52] U.S. Cl. .................. 157/1.28; 157/1.24; 157/14; 157/16; 157/1.2
[58] Field of Search ............ 157/1.17, 1.2, 1.22, 157/1.24, 1.26, 1.28, 14, 16

[56] References Cited

U.S. PATENT DOCUMENTS 3,086,578  4/1963  Breazeale et al. .................. 157/1.24
4,047,553  9/1977  Kotila ................................ 157/1.24

FOREIGN PATENT DOCUMENTS

0358729  7/1989  European Pat. Off. .

Primary Examiner—D. S. Meislin
Attorney, Agent, or Firm—Baker, Maxham, Jester & Meador

[57] ABSTRACT

A mounting device for automative tires having a rotationally driven holder for gripping a wheel rim and a pressing device mounted on a stand for pressing the tire bead away from the horn of the wheel rim. The device has two arms guided by means of sliding bushings on a column so they can be moved laterally toward and away from each other. These arms are hinge connected at their rear ends to the sliding bushings so they can be pivoted by a motor drive. A pressure element that acts on the tire wall next to the horn of the wheel rim is mounted on the front free end of each arm. The two arms are designed so their length can be adjusted by telescoping. A linear drive whose adjustment element has a coupling element that automatically engages with the extensible inside part of the respective telescopic arm is mounted approximately in parallel above and below each telescopic arm.

19 Claims, 5 Drawing Sheets

MOUNTING DEVICE FOR MOTOR VEHICLE TIRES

FIELD OF THE INVENTION

This invention concerns a mounting device for automotive tires consisting of a rotationally driven holder for clamping a wheel rim and a pressure device mounted on a stand for pressing the tire bead out of the horn of the wheel rim, the device having two arms which can be advanced laterally toward each other by means of a motor drive and are guided on a column by means of sliding bushings.

BACKGROUND OF THE INVENTION

European patent application 0,358,729 discloses a related device for mounting a motor vehicle tire on a wheel rim or removing it from a wheel rim, whereby the bearing support for the wheel rim has a pneumatic rotating drive and clamp arms that are spread by means of a pneumatic drive with respect to the upright axis which is aligned at a slight angle to the vertical and have pressure parts on their free ends that press from the inside against the bed of the wheel rim with a spreading motion. Due to the offset angle of the clamp arms, the wheel rim is automatically centered on the slightly inclined upright axis of the bearing support. The two arms of the pressure device which have the pressure elements are mounted on a vertical column so they pivot in the horizontal plane and are arranged so they can be advanced toward each other by means of a compressed air cylinder in the axial direction of the column. Each arm consists of a holder mounted on a column guide, where the holder is in the form of a sliding bushing, and a lever that is mounted with one end in this holder so it can rotate and has a pressure roll on its free end. A pressure cylinder arranged in the holder acts approximately on the middle section of the lever and exerts a compressive force on the lever across the longitudinal axis of the arm and thus also on the pressure roll, so the two levers of the two arms each execute a limited pivoting motion about their end bearings. At the upper end of the machine stand a buckling arm is mounted so it can be pivoted vertically and has a hook-shaped lifting element on its free end that acts on the tire bead from beneath when the buckling arm is moved by an operator and the lifting hook is pulled by hand over the horn of the wheel rim. By rotating the bearing support, the tire bead is released from the rim by this lifting hook. The primary disadvantage of this known mounting device is the inadequate adaptability to different types of tires and wheel rims. In addition, operation of the individual function groups requires a considerable amount of experience and skill on the part of the operator.

U.S. Pat. No. 4,047,553 discloses a mounting device for pneumatic tires having a column-like bearing support on a rigid bed with a conical clamping wheel held on the threaded spindle so it can rotate in order to secure the bowl of the tire. A vertical stand is adjustable in height like a telescope by means of a pressure cylinder and has two horizontal arms, the ends of which each have a conical pressure roll mounted on them. The pressure rolls can be advanced up to one side wall or the other in succession by means of vertical movements of the telescoping stand in order to force one tire bead or the other away from the horn of a wheel rim. This known mounting device also requires skilled personnel and can be used with different tire sizes and different types of wheel rims only to a limited extent. A similar mounting device for tires is also known from U.S. Pat. No. 3,086,578.

Another important disadvantage of all the known mounting devices is that the pressure elements that are designed as conical rolls made of plastic, for example, act directly on the relatively sensitive side walls of the tire in the pressing operation, which can lead to imperceptible damage to the interior of the tire, especially the radial body. Such damage must be avoided at all costs because it can have a very negative effect on the driving safety of the motor vehicle and can lead to sudden blowout of the tire at high speeds.

SUMMARY OF THE INVENTION

The purpose of this invention is to create a widely adaptable mounting device that can be adjusted easily and rapidly to different tire sizes and different types of wheel rims and makes it possible to largely automate the individual mounting operations and also rules out the possibility of damage to the tire walls during the pressing operation.

This problem is solved according to this invention by the fact that the two arms of the pressing device are of telescopic construction, and the guide column for the two arms is aligned at an acute angle to the vertical. A pressure cylinder whose piston rod acts on a coupling element that automatically engages the extensible inside part of the telescopic arm when the pressure cylinder is activated is mounted on the guide element of each arm sliding on the column.

According to one embodiment of this invention, one guide system is used to achieve the combined pivoting and forward motion of each of the two telescopic arms and connects the proximal end of the telescopic arm to the sliding bushing and allows a force-guided, movement of this end of the arm.

Another embodiment of this invention includes an axially parallel polygonal guide rod can be arranged behind the cylindrical guide column in the stand which is aligned so it is axially parallel to the bearing support, in which case the sliding bushings have rear projections that extend around the guide rod in the sliding seat. With this double guidance a highly stable sliding mount of the telescopic arms is achieved so the high forces and moments that occur in pressing can be transferred to the column.

According to a refinement of this invention, an angled hand lever is mounted on the stand and can be designed so it can be pivoted about its middle axis and can be telescoped outward.

Another alternative embodiment has a lifting device with a three-part buckling arm on whose free end is attached a double arm with one lifting tool on each so that it can be rotated by 180°.

Yet another embodiment of this invention is characterized in that a spring-loaded rotating disk is arranged so it can slide in the axis of the bearing support. This spring disk assures large-area contact and thus secure support for the wheel at right angles to the axis of the support. Due to the fact that the disk can be shifted against the force of a helical spring, the wheel rim can be positioned in the optimum location with respect to the clamping arms, so the pressure pieces of the clamping arms always come to rest against a smooth inside wall part of the bed of the wheel rim and thus secure and reliable mounting of the wheel rim on the bearing support is assured.

BRIEF DESCRIPTION OF THE DRAWING

The objects, advantages and features of the invention will be more clearly perceived from the following detailed description, when read in conjunction with the accompanying drawing, in which.

DESCRIPTION OF THE PREFERRED EMBODIMENTS

Figures 1, 3:
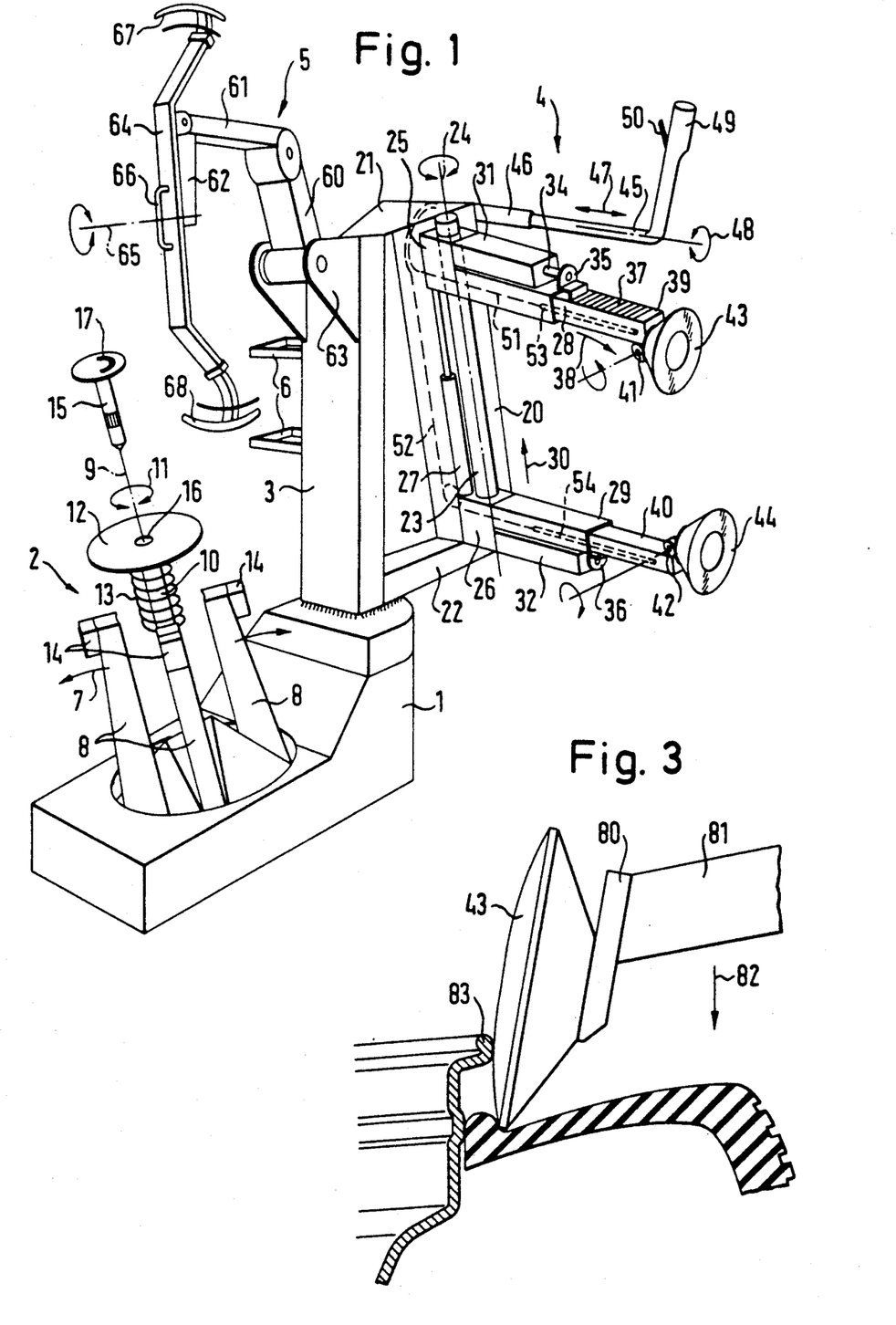
FIG. 1 is a schematic perspective diagram of the mounting device.
FIG. 3 is an enlarged side view of another conical pressure roll during a pressing operation.

The mounting device shown in FIG. 1 includes rigid stable base 1 which accommodates drive elements and controlling devices in the interior. The front lower part of base 1 contains bearing support 2 and stand 3 is positioned on the elevated rear part having pressure device 4 offset toward the rear at the side and lifting device 5 on the front end. Several areas 6 for depositing small parts are attached to the side wall of the stand.

Bearing support 2 contains four clamping arms 8 that can be spread out in the direction of arrows 7 and are arranged so they are offset by an angle of 90° around upright axis 9 that is inclined by an acute angle with respect to the vertical. Clamping arms 8 are spread apart by means of a compressed air motor that is accommodated in base 1 and sets bearing support 2 in rotation about upright axis 9 during a pressing and lifting operation. Central supporting column 10 is mounted so it can be shifted longitudinally in the bearing support and can be rotated in the direction of arrow 11. On the free end of supporting column 10 there is disk 12 that can be inserted manually together with supporting column 10 against the force of spring 13. With the spreading motion of the arms, pressure pieces 14 on the upper ends of the clamping arms rest against the inside wall of the bed of the wheel rim of a motor vehicle wheel which has been placed on disk 12 and manually pushed into the appropriate position. To secure the wheel on disk 12, clamping mandrel 15 with a mating disk attached to it and a rubber clamping sleeve (not shown) are inserted through the axial bore of the wheel hub into hole 16 of disk 12 and supporting column 10 and is secured by turning it around with hand lever 17.

Figure 2:
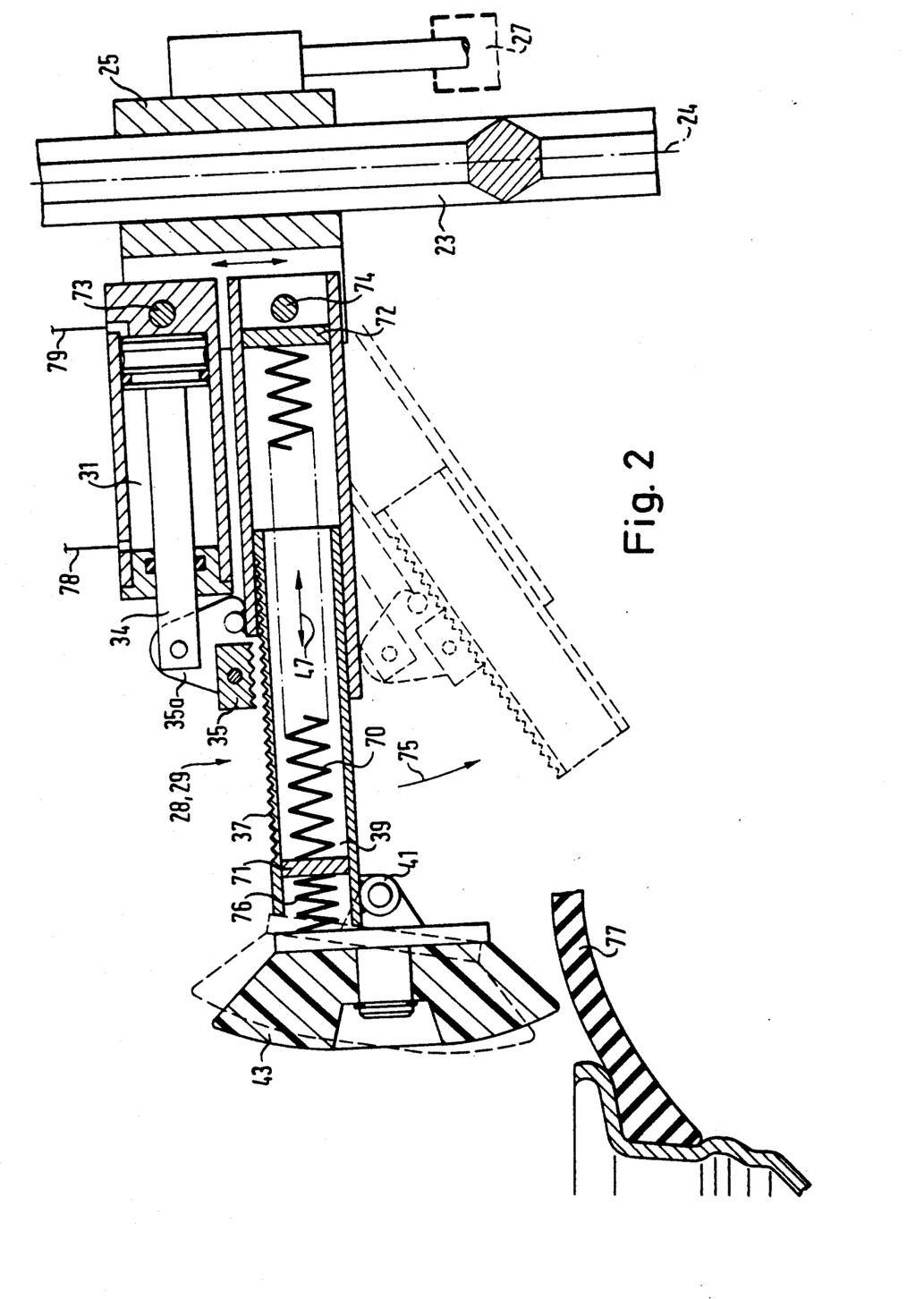
FIG. 2 shows one possible embodiment of the telescopic arm of the mounting device illustrated in FIG. 1.

Pressing device 4 includes supporting frame member 20 that is attached at both its ends between cross parts 21, 22, each on the rear side of stand 3 and support 1, and is arranged behind the stand on the side. In the interior of this frame member 20 there is guide column 23 whose axis 24 runs parallel to the upright axis 9 of bearing support 2. Two guide bodies 25, 26 can be guided on guide column 23 by means of a linear drive, which is compressed air cylinder 27, with upper and a lower telescopic arm 28, 29 connected to the front side of the compressed air cylinder. Due to the compressed air acting on compressed air cylinder 27, telescopic arms 28, 29 are shifted in the direction of arrows 30 and thus in the direction of longitudinal axis 24. The two telescopic arms can be turned about axis 24, preferably synchronously by hand, so they can assume a radial position to upright axis 9 of the bearing support when a motor vehicle wheel is placed on the support and secured there. Above upper telescopic arm 28 and below lower telescopic arm 29 a linear drive, which is designed here as a hydraulic cylinder or compressed air cylinder 31, 32, is hinge-connected to respective guide body 25, 26 and aligned approximately parallel to the respective telescope arm 28, 29. Hook-shaped coupling element 35, 36 is hinge-connected to the front end of respective piston rod 34 by way of pivoting intermediate element 35a (FIG. 2). At the start of an outward movement of the piston rods, this hook-shaped coupling element automatically engages with cogged profile 37 which is designed on the outside of inside part 39, 40 that can be pulled out of each telescopic arm 28, 29. Intermediate element 35a is mounted on the front end of the outside part of each telescopic arm 28, 29 so it can be pivoted to a limited extent around a cross pin. Due to the hydraulic medium acting on compressed air cylinders 31, 32, the respective telescopic arm is shifted in the direction of arrow 38 on a path that curves upward in an arc after hook-shaped coupling element 35 engages in cogs 37 of upper telescopic arm 28 or hook-shaped coupling element 36 engages in the cogs (not shown) provided on the lower side of lower telescopic arm 29. One holder 41, 42 is attached to the free end of each inside part 39, 40 and a pressure roll 43, 44 is mounted on each holder so it can be pivoted about transverse axes against the force of a spring (not shown). The size of the opposing pivoting motions of pressure rolls 43, 44 is limited by stops (not shown). Pressure rolls 43, 44 are made of a high-impact plastic and have a circular curved face and a rear conical jacket.

Due to the telescoping design of the two pressure arms, the operator can accurately adjust the length of the arms and thus the position of the respective pressing element on the diameter of the wheel rim by manual extension of the telescopic arm so the respective pressure elements press on the tires directly next to the wheel rim, i.e., directly adjacent to the tire bead. Not only does this assure an optimum pressure even with different tire sizes and wheel rim sizes but also damage to the tire walls, especially the casing or carcass, is safely prevented by the pressure rolls. Due to the combined pivoting and forward movement of the respective pressure element, its pressure acts on the tire during the entire pressing operation in the area of the relatively insensitive saddle of the bead without involving the pressure-sensitive side walls of the tire.

This pressure is promoted, for example, by a hinge connection that can be pivoted within given limits and is provided on the pressure roll holder on the extensible part of the telescopic arm, in which case this pressure roll holder can preferably be connected in an articulated mount to the telescopic arm with an upward or downward offset and can be held in its starting position by means of a spring.

Due to the axial parallel arrangement of a linear motor designed as a hydraulic cylinder next to, i.e., above and/or below the respective telescopic arm, and due to the automatically drawn-in coupling of its piston rod with the extractable inside part of the telescopic arm in combination with the bearing system provided on the rear end of the arm, the effect achieved is that the desired combination of a pivoting and forward movement of the pressure element is accomplished by actuation of only one drive unit, namely, the hydraulic cylinder.

Angled hand lever 45 that can be shifted axially (arrow 47) by hand in holder 46 attached to frame member 20 and can be turned about the longitudinal axis (arrow 48) is used for synchronous extraction of the two inside parts 39, 40 of telescopic arms 28, 29. Pressure switches 50 with which the compressed air to compressed air cylinder 27 or 31, 32 is controlled are provided on handle 49. Hand lever 45 is also connected by two push and pull cables 51, 52 to one pusher rod 53, 54 each, so inside parts 39, 40 of telescopic arms 28, 29 can be extracted by a corresponding amount from the respective outside part of the arm, and vice versa.

The telescoping part of this hand lever is mechanically connected, e.g., by means of flexible thrust elements (Bowden wire levers) or by means of hydraulic lines to the two telescoping parts of the telescopic arms, so a longitudinal movement of this hand lever leads to a synchronous drawing in or telescoping motion of the two movable inner parts of the telescopic arms. Preferably, hand switches are provided on this hand lever so that when the switches are operated, the pressure cylinders mounted on the telescopic arms are acted on by a hydraulic medium, especially compressed air. In addition, the control lever can be mounted in a horizontal plane so it can be pivoted about an upright axis on the machine stand, which is favorable from the standpoint of ease of operation.

Lifting device 5 contains a buckling arm formed by three individual arms 60, 61, 62, the first of which (60) is mounted on bracket 63 on the upper front end of stand 3 so it can be pivoted about a transverse axis. A spring (not shown) holds the buckling arm in its upper retracted resting position. Double arm 65 is mounted on the free end of third arm 62 so it can be rotated 180° about axis 65 by means of handle 66 and can be locked in one end position or another. Lifting tool 67, 68 is provided on each bent-back end of double arm 64, so one lifting tool is made of a high-impact plastic for assembly of light metal wheels and the other consists of a suitable metal such as steel for mounting steel rims.

The three parts of the buckling arm are connected in an articulated manner about horizontal axes where one spring holds the buckling arm automatically in a retracted resting position. Owing to the multiple articulations in this buckling arm, the lifting element selected in this case can be positioned with a high degree of accuracy on the respective tire bead even when working with wheel rims of different sizes. Use of two lifting elements that can be selected permit optimum adjustment to the different types of wheel rims, e.g., steel rims and aluminum rims.

The telescopic arm shown in an enlarged longitudinal section in FIG. 2 corresponds in its basic design to telescopic arms 28, 29 of the mounting device according to FIG. 1. However, guide column 23 has a hexagonal cross section so guide body 25 cannot be pivoted about column axis 24. Hook-shaped coupling element 35 in the embodiment in FIG. 1 is designed here as a cogged element and is mounted so it can be pivoted on triangular intermediate element 35a that is hinge-connected to the free end of piston rod 34 and also to the end of the outer part of the arm. In inner part 39 of the arm there is a linear drive in the form of compression spring 70 which is supported with its front end on transverse wall 71 of inside part 39 and its rear end rests on transverse wall 72 in the interior of the outer part of the arm. Compressed air cylinder 31 and the outer part of the arm are each supported on a cross pin 73, 74 in a recess in guide body 25. Cogged element 35 automatically engages with cogs 37 when piston rod 34 moves out, as in the embodiment according to FIG. 1, whereupon a pivoting motion of the supporting arm in the direction of arrow 75 begins. Holder 41 is attached to the lower wall of inside arm 39 and pressure roll 43 is mounted on the holder so it can pivot about a cross pin into the position indicated with a dotted line. Compression spring 76 is stretched between the rear wall of pressure roll 43 and transverse wall 71 in inside arm 39. This compression spring 76 counteracts a swinging motion of the pressure roll after it is positioned on side wall 77 of the tire. Hydraulic medium is supplied to the compressed air cylinder through two connecting lines 78 and 79.

The variant illustrated in FIG. 3 shows pressure roll 43 with its conical rear part rigidly mounted on flap 80 which is in turn rigidly connected to the inclined end of supporting arm 81. In this design supporting arm 81 moves approximately vertically in the direction of arrow 82, and the bulging face of inclined pressure roll 43 slides along the outside edge of horn 83 of the wheel rim and in doing so presses the tire bead out of its position in the horn of the wheel rim.

With the mounting device described above, one pressure cylinder can be provided for each telescopic arm 28, 29. Alternatively, another control element such as a spindle drive, a toothed rack, etc., instead of the single pressure cylinder 27 shown in FIG. 1, can be employed to adjust the height of telescopic arms 28, 29 in order to be able to perform the height adjustment separately for each telescopic arm. The same thing is also true of pusher rods 53, 54, which can be replaced by other suitable linear drives such as hydraulic medium cylinders, toothed racks, spindle drives, etc. The type of automatically drawn-in coupling of piston rod 34 to movable inside parts 39, 40 of telescopic arms 28, 29 is not limited to the embodiments illustrated in FIGS. 1 and 2 but instead can also be designed otherwise, e.g., by means of clamping elements. Moreover, the variants shown in FIGS. 1 to 3 can also be combined with regard to the individual parts.

In order to use only a single type of energy, namely, compressed air, for the various types of linear drives and also be able to utilize the known advantages of hydraulic servo drives at the same time, it is advantageous to design the linear drives as combined compressed air-hydraulic cylinders or provide at least a hydropneumatic converter in the pressure device to convert the air pressure supplied from the outside to a fluid pressure that is supplied to the various control cylinders by way of an internal line system.

Figure 4:
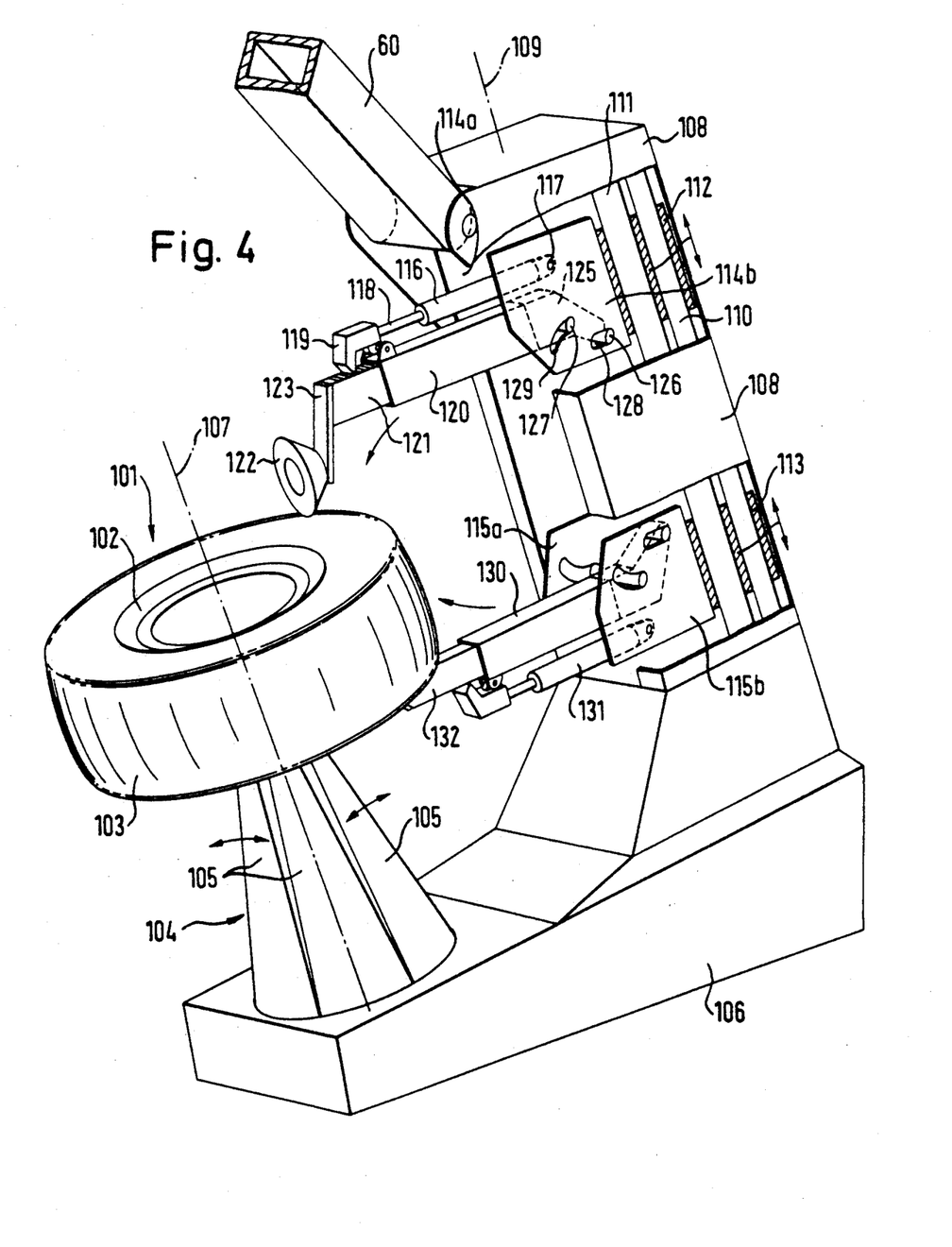
FIG. 4 shows another mounting device in a schematic perspective view.

With the mounting device illustrated in FIG. 4, motor vehicle wheel 101 with rim 102 and tire 103 that is to be removed is attached to supporting structure 104 which consists of several supporting arms 105 that can be spread apart in the direction of the arrows, plus a drive motor in base 106 of the device for spreading and rotating motor vehicle wheel 101 about upright axis 107. The upright axis is inclined at an angle with respect to the vertical in order to facilitate the placement of even heavy motor vehicle wheels on the spring-loaded plate (not shown) of supporting structure 104 which corresponds in structure to the embodiment shown in FIG. 1. This structure also has a compressed air motor (not shown) as the drive unit for spreading supporting arms 105 and for turning motor vehicle wheel 101.

Stand 108 whose longitudinal axis 109 is also inclined by an acute angle with respect to the vertical and runs parallel to upright axis 107 of supporting structure 104 is attached to the rear elevated part of base 106. In the rear part of this stand there is guide rod 110 with a square or rectangular cross section and in front of this there is cylindrical guide column 111 mounted axially parallel with respect to each other and axis 109 of the stand. Two sliding or guide bushings 112, 113 can be shifted longitudinally on guide elements 110 and 111 and are guided in such a way that they are secured against twisting, whereby each guide bushing 112, 113 is connected to a linear drive, e.g., a hydropneumatic control cylinder that moves the respective guide bushings individually or together in the opposite direction along axis 109 after a suitable hydraulic medium has acted on it. This process was described in detail for the mounting device according to FIG. 1 and is also applicable here. Upper and lower pairs of plates 114a, 114b and 115a, 115b are mounted on the front side of each sliding busing 112, 113 and each pair of plates encloses a space in the middle. Hydraulic cylinder 116 is hinge connected between upper plates 114a, 114b in this interspace by means of bearing pin 117 whose rod 118 acts on catch 119. In addition, telescopic arm 120, whose extensible arm part 121 has conical pressure roll 122 on inclined plate 123, is mounted between the two upper arms. Inclined supporting part 125 to which two cross pins 126, 127 are attached by welding, for example, is mounted on the rear end of telescopic arm 120. Each of these cross pins has a running roll on each end running in longitudinal holes 128, 129 in each of the two plates 114a, 114b.

Figure 5:
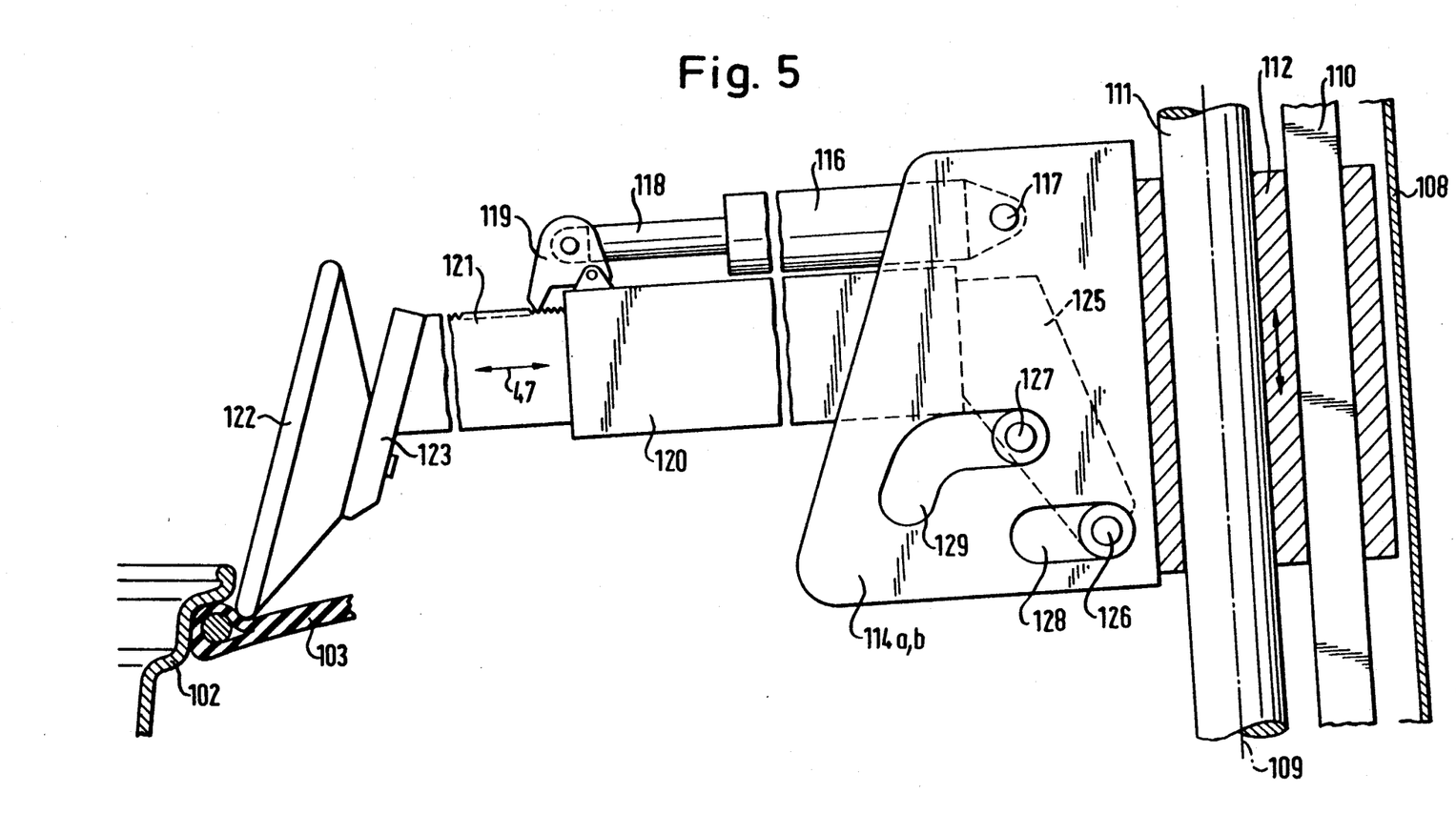
FIG. 5 and 6 each reveal an enlarged schematic side view of a telescopic arm.

As FIG. 5 shows, upper longitudinal hole 129 has a section that runs approximately across axis 109 that develops into a curved section pointing downward. Lower longitudinal hole 128 is approximately linear and runs across axis 109 of the stand.

As shown especially in FIG. 4, telescopic arm 130 is also mounted over two cross pins in longitudinal holes between lower plates 115a, 115b and hydraulic cylinder 131 provided for the telescopic arm acts with its rod on a catch which, like catch 119, is mounted on the outside of the holding part of the telescopic arm so it can pivot. The individual parts of this telescopic arm 130 and its mount correspond to those of upper telescopic arm 120.

Figure 6:
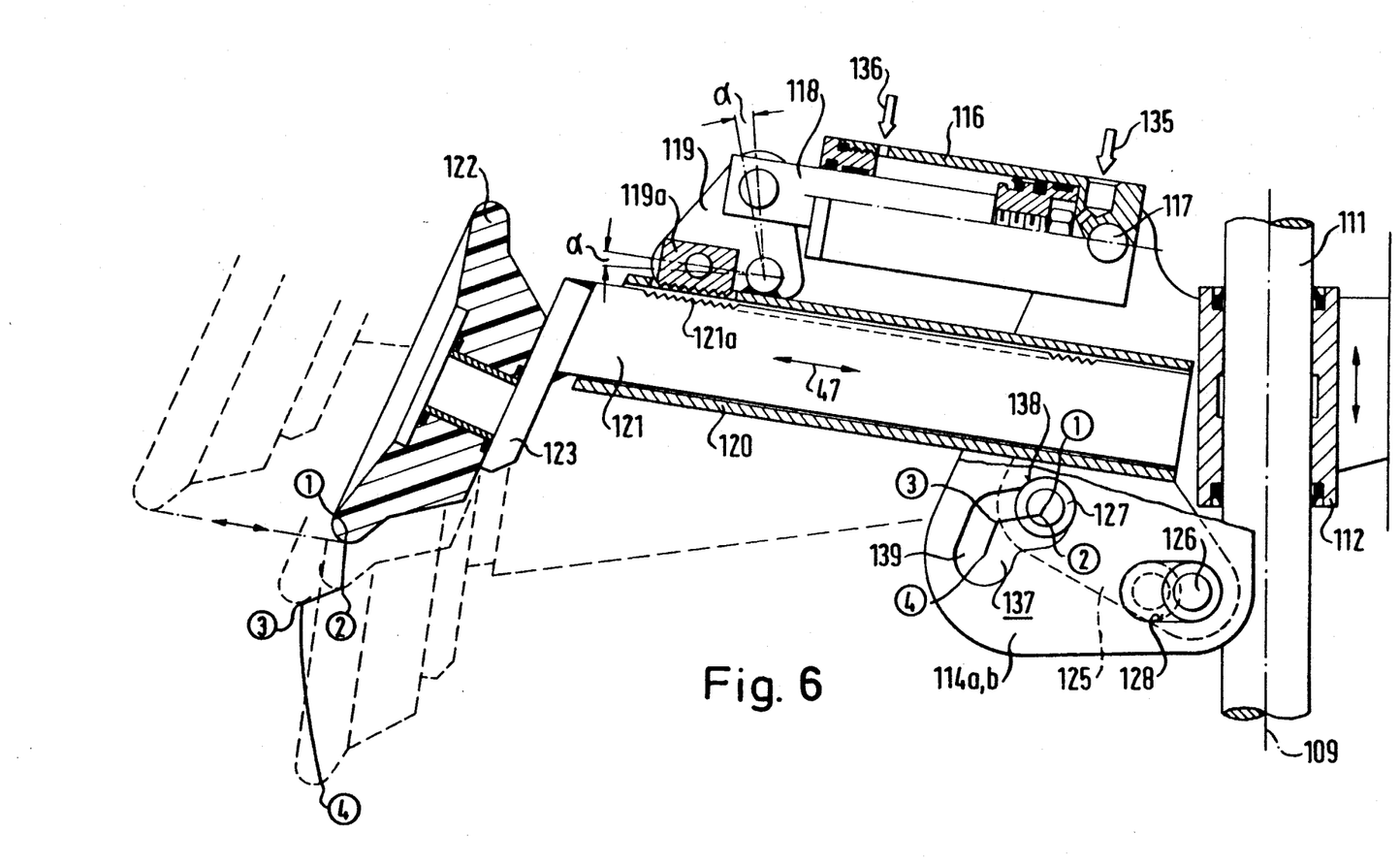

The embodiment according to FIG. 6 corresponds largely to telescopic arm 120 shown in FIG. 5 so the same parts are also labeled with the same numbers. In the embodiment shown here, control cylinder 116 for telescopic arm 120 is a hydropneumatic unit which receives hydraulic fluid for the power stroke through connection 135 and receives compressed air for the return stroke through connection 136. In this way an adequately strong power stroke for effective pressure, even against a resistant tire bead from its seat on the tire rim, and an accelerated retraction motion of pressure roll 122, are achieved. Another variant consists of the form of upper longitudinal hole 137 which consists of a total of three sections angled toward each other, where first section 138 runs upward at an angle approximately parallel to third section 139 in FIG. 6. Due to this form of longitudinal hole 137, rollers 127 are guided on a three-part path which is shown in FIG. 6 by a thicker line and numbers (1) to (4). This special path of motion leads to a corresponding three-phase motion of the pressure roll, the course of which is also indicated by a bold line and numbers (1) and (4). The effective lower edge of the pressure roll is indicated with a dotted line in the respective end points of the individual phases of motion (1) to (4). Furthermore, the tilting motions in angle range $\alpha$ of coupling element 119 during and after engagement of its catch 119a in cogs 121a of inside part 121 of the telescopic arm are also shown. Catch 119a engages in a cutout in the upper wall of outer part 120 of the arm.

The mounting device described above is used as described below.

After motor vehicle wheel 101 is placed on base 104 and the wheel rim is secured in position by spreading supporting arms 105, telescopic arms 120, 130 are extended by the operator in sychronization by cables (not shown) or other suitable means until upper and lower pressure rolls 122 are directly above and below the respective wheel rim. Operating a switch causes a compressed air valve to function to move the two telescopic arms individually or simultaneously toward each other, whereby both arms are guided on guide column 111 and polygonal rod 110. This opposing transverse motion of telescopic arms 120, 130 is automatically concluded as soon as pressure rolls 122 are supported on tire 103 directly next to horn 102 of the wheel rim. Then the two hydraulic cylinders are supplied with a hydraulic medium either individually or together, which leads to double automatic engaging of coupling elements 119 in the upper and lower cogs of extensible arm parts 121, 132. Another extension motion of piston 118 causes the two tire beads to be pushed out of their seat, while each telescopic arm 120 executes a pivoting motion about cross pin 126 or its roller as the axis of rotation in this phase. As soon as the respective tire bead is released somewhat from its seat on horn 102 of the wheel rim, the entire telescopic arm 120 with its cross pins and the rollers mounted on it is shifted in longitudinal holes 128, 129 by another extension motion of rod 118, whereby composite pivoting and forward advance motion of pressure roll 122 is achieved by means of the coordinated shapes of these two longitudinal holes, where the path of these movements corresponds approximately to the contour of the wheel rim. The effect achieved by this combination pivoting motion and forward motion is that during the entire pressure operation the point of action of roll 122 directly next to the tire bead as shown in FIG. 5 is retained even when the respective pressure roll 122 penetrates relatively far into the bed of the wheel rim and there is no pressure stress acting on the sensitive side walls of the tire.

Preferably the guide system which achieves the combined pivoting and forward motion of the two telescopic arms contains two cross pins attached to the end of the arm and at least one vertical plate mounted on the sliding bushing with an upper angled, elongated hole and a lower approximately linear elongated hole, in which the cross pins are guided in the plate. A greater torsional rigidity and thus a greater stability of the guide system is achieved when two parallel plates are attached to the side of each sliding bushing with the telescopic arm that has a rectangular cross section held between the plates so it can move within the dimensions determined by the elongated holes, and also the linear drive which is designed as a hydraulic cylinder is connected in an articulated mount here. Due to this design of the guide system there is a movement of the pressure element which is designed as a plastic conical roll with a predominantly pivoting component of motion when the hydraulic cylinder is actuated in a pressing phase because the upper cross pin runs in the approximately horizontal part of the elongated hole while the lower cross pin remains in the rear section of the elongated hole provided for it. Only in a second phase of the pressing operation is there a motion of the pressure element whereby the forward component of motion is predominant in comparison with the pivoting component of motion in order to push the pressure element into the mouth of the wheel rim. In this second phase of motion, the upper cross pin runs in the bent part of the upper elongated hole, and the lower cross pin is shifted horizontally in its elongated hole. An even more favorable forward motion and pivoting path of the pressure element can usually be achieved if the upper elongated hole contains a total of three sections that are angled with respect to each other, where the effective section in the first phase of motion of the telescopic arm, i.e., in the pressure phase, runs upward at an angle in order to impart to the pressure element a motion directed more normal to the side wall of the tire. The preceding discussion concerns the upper telescopic arm but applies to the same extent also to the lower cross arm.

This invention is not limited to the practical examples illustrated here but instead can also be used with other embodiments where pressure arms equipped with pressure rolls are mounted on an upright stand. This invention can especially also be used with a mounting device with which each telescopic arm and the respective hydraulic cylinder are individually hinge-connected to a guide body which is guided so it can rotate on a guide column arranged in a hollow support attached at the side behind the machine stand in such a way that its longitudinal axis runs approximately parallel to the upright axis of the base. Through this arrangement of the guide column, a mount of the two telescopic arms that permits them to pivot about the guide column in the transverse plane of the arms is achieved. This also yields the advantage that the two telescopic arms can be pivoted out of the working area at the side in mounting large tires, so a sufficiently large free space is available for unhindered support and securing of the motor vehicle tire. In addition, individual parts or component groups of the embodiments described here can be combined or exchanged. For example, the extending motions of the two telescopic arms according to FIG. 5 and 6 can be executed with the help of hand lever 45, 49 shown in FIG. 1 and cables 51, 52, or by means of other manual or motor-driven adjusting devices.

What is claimed is:

1. A mounting apparatus for motor vehicle tires having beads and side walls and mounted to a wheel rim having a horn portion, said apparatus comprising:
    a base;
    a bearing support mounted to said base and having an upwardly extending axis and a rotationally driven holder for clamping the tire rim thereto;
    a stand upwardly projecting from said base;
    a pressure device mounted on said stand, said pressure device being adapted for applying pressure sufficient for pressing the tire bead away from the horn of the wheel rim;
    two motor-driven telescopic arms, each said telescopic arm having a base portion coupled at the proximal end to said pressure device and having an extensible portion fitted telescopically to said base portion, said each telescopic arm being adjustable in length;
    a pressure element coupled to the distal end of each said telescopic arm adapted to act on a tire wall next to the horn of the wheel rim;
    a column mounted to said stand and having a generally upwardly projecting axis;
    sliding bushings on said column, the proximal ends of each said telescopic arm being pivotably connected to a respective said sliding bushing, said sliding bushings guiding said telescopic arms in motion toward and away from each other;
    a motor drive for applying force sufficient for pivoting said telescopic arms on said sliding bushings;
    a linear drive coupled to said motor drive and pivotably coupled at the proximal end to each said respective sliding bushing, each said linear drive having a linearly moving element coupled to said base portion of said respective telescopic arm for adjusting the linear and angular displacement of said respective telescopic arm with respect to said column; and
    a coupling element mounted to each said moving element for engaging said extensible portion of said respective telescopic arm when said respective linear drive is activated.

2. The mounting apparatus recited in claim 1, wherein each said telescopic arm is pivotally connected to said respective sliding bushing by means of a system of one or more guided pivots that force a combined pivoting and forwarding motion of said each telescopic arm responsive to extension of said respective linearly moving element, whereby said pressure element is pressed into the bead of the tire after an initial release of the tire bead from the horn of the tire rim.

3. The mounting apparatus recited in claim 2, wherein each said guided pivot system comprises:
    two parallel plates attached to each said sliding bushing wherein said telescopic arms have substantially rectangular cross-sections and are held between said respective pair of parallel plates; and
    a supporting element attached to the proximal end of each said telescopic arm and coupled to said respective pair of parallel plates by means of two cross pins attached to said supporting element, each said cross pin having rollers on both ends thereof, each said roller being engaged and guided in one of two longitudinal slots formed in each of said respective pair of parallel plates.

4. The mounting apparatus recited in claim 3, wherein each said parallel plate includes one said longitudinal slot that runs linearly in each said parallel plate, and a second said longitudinal slot that consists of a plurality of linear sections, each arranged at an angle to another adjacent said section.

5. The mounting apparatus recited in claim 1, wherein each said linear drive is a hydraulic cylinder having its linearly moving element coupled to said extensible portion of said telescopic arm by means of said coupling element, said coupling element being connected in an articulated joint to the distal end of said base portion of said telescopic arm.

6. The mounting apparatus recited in claim 5, wherein:
    each said linear drive is a hydraulic cylinder having a linearly moving element that is a piston rod and further comprises;
    a guide body to which said articulated joint is individually connected; and an intermediate element on which each said coupling element is mounted, said intermediate element being connected by means of said articulated joint to the distal end of said piston rod and being connected to said base portion of said telescopic arm.

7. The mounting apparatus recited in claim 1, and further comprising a control lever coupled to said extensible portions of said telescopic arms and coupled to said stand, said control lever being movable by an operator, the length of said two telescopic arms being adjustable in synchronization by means of said control lever.

8. The mounting apparatus recited in claim 7, wherein said control lever is coupled to two push-pull cables and pusher rods which are each in turn coupled to said extensible portion of a respective said telescopic arm.

9. The mounting apparatus recited in claim 7, each said telescopic arm further comprising second linear drive means for extending said extensible portion thereof.

10. The mounting apparatus recited in claim 9, and further comprising:
pressure switches on said control lever;
control elements connected to said pressure switches;
means for moving said arms toward and away from each other;
said arm moving means and said linear drives comprising hydraulic cylinders, said pressure switches and said control elements being connected to said hydraulic cylinders for control thereof.

11. The mounting apparatus recited in claim 7, and further comprising:
pressure switches on said control lever;
control elements connected to said pressure switches;
means for moving said arms toward and away from each other;
said arm moving means and said linear drives comprising hydraulic cylinders, said pressure switches and said control elements being connected to said hydraulic cylinders for control thereof.

12. The mounting apparatus recited in any one of claims 1 to 4, wherein said column is cylindrical and each said telescopic arm is coupled to two guide bodies disposed to pivot about their longitudinal axes on said cylindrical column and each said telescopic arm is adapted to be adjusted individually in height by means of a second linear drive connected between said two guide bodies.

13. The mounting apparatus recited in any one of claims 1 to 4, and further comprising a guide element in said column, the longitudinal axis of said guide element being approximately parallel to said upwardly extending longitudinal axis of said bearing support.

14. The mounting apparatus recited in any one of claims 1 to 4, wherein each said pressure element comprises a pressure roll formed as a conical disk with a bulging face having an axis and being mounted on a holder on the distal end of said extensible portion of each said telescopic arm, said holder being pivotable about a transverse axis.

15. The mounting apparatus recited in claim 14, wherein each said pressure roll has a conical rear side obverse said bulging face and is attached to an incline plate that is in turn mounted on the end of said extensible portion of a respective said telescopic arm.

16. The mounting apparatus recited in any one of claims 1 to 4, and further comprising a lifting device coupled to said stand, said lifting device including a multi-jointed three-part buckling arm having a double arm mounted rotatably on its distal end, said double arm having one lifting element on each end and being rotatable by at least 180° and said double arm having locking means for locking it in two extreme rotational positions.

17. The mounting apparatus recited in any one of claims 1 to 4, and further comprising a spring-loaded rotatable disk coupled to said bearing support by means of a spring so that said disk is slidable in and rotatable about said upwardly extending bearing support axis.

18. The mounting apparatus recited in claim 17, and further comprising a safety rod coaxially engaged by insertion into a hollow cylindrical axis in said bearing support, whereby said tire rim is safely restrained to said bearing support upon failure of clamping thereof by said rotationally driven holder.

19. The mounting apparatus recited in any one of claims 1 to 4, wherein said linear drives are configured as combined compressed air and hydraulic cylinders.

* * * * *